United States Patent
DiGuiseppi et al.

(10) Patent No.: US 7,803,608 B2
(45) Date of Patent: Sep. 28, 2010

(54) INTEGRATED FILTRATION AND DETECTION DEVICE

(75) Inventors: James L. DiGuiseppi, Durham, NC (US); Diederik Engbersen, Ecully (FR); Scott R. Jeffrey, Clarksville, VA (US); John Walsh, Durham, NC (US)

(73) Assignee: Biomerieux, Inc., Durham, NC (US)

( * ) Notice: Subject to any disclaimer, the term of this patent is extended or adjusted under 35 U.S.C. 154(b) by 343 days.

(21) Appl. No.: 10/084,578

(22) Filed: Feb. 27, 2002

(65) Prior Publication Data

US 2002/0127630 A1 Sep. 12, 2002

Related U.S. Application Data

(60) Provisional application No. 60/272,233, filed on Feb. 28, 2001.

(51) Int. Cl.
*C12M 1/34* (2006.01)
(52) U.S. Cl. ............... 435/288.7; 435/297.2; 435/297.5; 435/308.1
(58) Field of Classification Search ............ 435/34, 435/29, 287.1, 283.1, 288.7, 297.2, 297.5
See application file for complete search history.

(56) References Cited

U.S. PATENT DOCUMENTS

| 4,036,698 A | 7/1977 | Bush et al. ............... 195/103.5 |
| 4,215,198 A | 7/1980 | Gordon ........................ 435/31 |
| 4,640,777 A | 2/1987 | Lemonnier ................ 210/433.2 |
| 4,643,197 A * | 2/1987 | Greene et al. ................ 600/575 |
| 4,829,005 A * | 5/1989 | Friedman et al. ......... 435/288.1 |
| 4,945,060 A | 7/1990 | Turner et al. ................. 435/291 |
| 5,094,955 A * | 3/1992 | Calandra et al. ......... 435/288.7 |
| 5,162,229 A | 11/1992 | Thorpe et al. ............... 435/291 |
| 5,164,796 A * | 11/1992 | Di Guiseppi et al. ........ 356/445 |
| 5,217,876 A * | 6/1993 | Turner et al. ................. 435/34 |
| 5,340,741 A | 8/1994 | Lemonnier ................. 435/291 |
| 5,545,834 A * | 8/1996 | Singh et al. ..................... 544/6 |
| 5,567,598 A | 10/1996 | Stitt et al. ...................... 435/29 |
| 5,856,175 A | 1/1999 | Thorpe et al. ............ 435/287.5 |
| 5,858,769 A | 1/1999 | DiGuiseppi et al. ...... 435/287.3 |
| 5,998,517 A | 12/1999 | Gentle, Jr. et al. ............. 524/92 |
| 6,838,292 B1 * | 1/2005 | Rajan et al. ................. 436/518 |
| 2001/0031494 A1 | 10/2001 | Hendel ..................... 435/287.1 |

FOREIGN PATENT DOCUMENTS

WO WO 9811250 A2 * 3/1998

\* cited by examiner

*Primary Examiner*—William H Beisner
(74) *Attorney, Agent, or Firm*—Myers Bigel Sibley & Sajovec, PA

(57) ABSTRACT

An integrated filtration and detection device for collecting and detecting the growth of microorganisms in a specimen includes a container defining a chamber therein. The container has an inlet and an outlet in fluid communication with the chamber. A filter is mounted in the chamber between the inlet and the outlet. A sensor is mounted in the chamber. The sensor is operative to exhibit a change in a measurable property thereof upon exposure to changes in the chamber due to microbial growth.

27 Claims, 5 Drawing Sheets

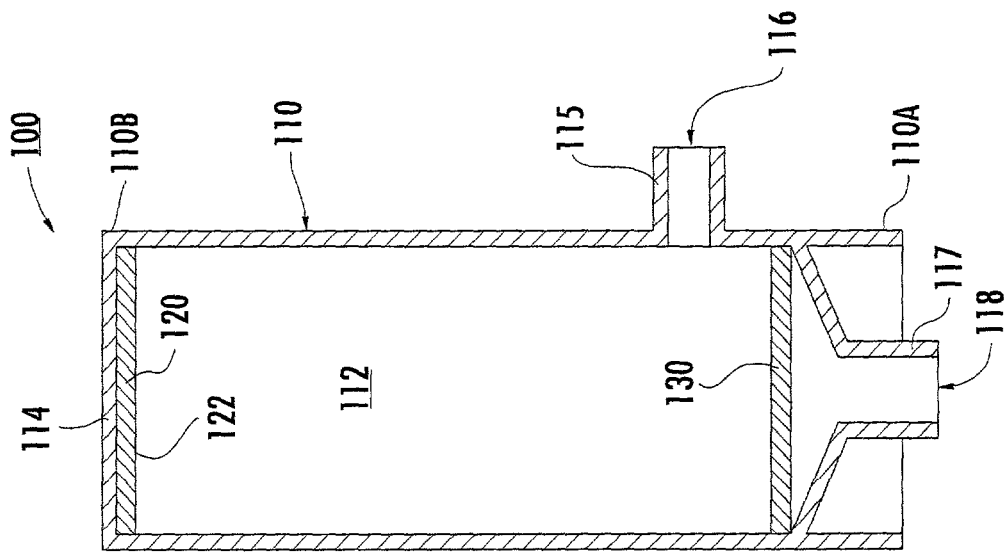
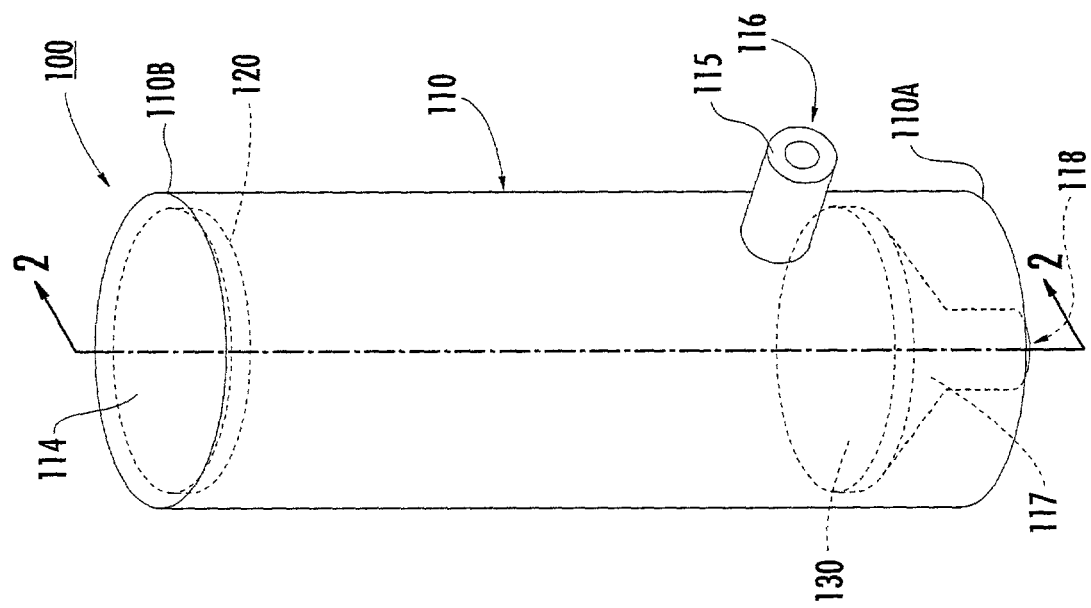

US 7,803,608 B2

INTEGRATED FILTRATION AND DETECTION DEVICE

RELATED APPLICATIONS

This application claims the benefit of priority of U.S. Provisional Application Ser. No. 60/272,233, filed Feb. 28, 2001, the disclosure of which is incorporated herein by reference in its entirety.

FIELD OF THE INVENTION

The present invention relates to detection devices, and, more particularly, to devices for detecting microbial growth in a specimen.

BACKGROUND OF THE INVENTION

It is often desirable or necessary to test fluid samples, such as liquid specimens, for contamination by live microorganisms. The presence of microbial contamination in clinical specimens is conventionally determined by culturing the specimens in the presence of nutrients and detecting microbial activity through changes in the specimen or the atmosphere over the specimen after a period of time.

It is often desirable to be able to test a specimen having a relatively large volume. Furthermore, it may be advantageous to increase the concentration of microorganisms in the specimen undergoing analysis so that changes in the specimen or adjacent atmosphere are intensified and thereby more easily and accurately detectable.

SUMMARY OF THE INVENTION

According to certain embodiments of the present invention, an integrated filtration and detection device for collecting and detecting the growth of microorganisms in a specimen includes a container defining a chamber therein. The container has an inlet and an outlet in fluid communication with the chamber. A filter is mounted in the chamber between the inlet and the outlet. A sensor is mounted in the chamber. The sensor is operative to exhibit a change in a measurable property thereof upon exposure to changes in the chamber due to microbial growth.

According to certain method embodiments of the present invention, a method for collecting and detecting the growth of microorganisms in a specimen includes providing an integrated filtration and detection device. The integrated filtration and detection device includes a container defining a chamber therein and having an inlet and an outlet in fluid communication with the chamber. A filter is mounted in the chamber between the inlet and the outlet. A sensor is mounted in the chamber and is operative to exhibit a change in a measurable property thereof upon exposure to changes in the chamber due to microbial growth. The specimen is passed into the chamber through the inlet, through the filter and out of the chamber through the outlet to collect the microorganisms on the filter. The measurable property of the sensor is detected.

Objects of the present invention will be appreciated by those of ordinary skill in the art from a reading of the figures and the detailed description of the preferred embodiments which follow, such description being merely illustrative of the present invention.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 1 is a perspective view of an integrated filtration and detection device according to embodiments of the present invention;

FIG. 2 is a cross-sectional view of the device of FIG. 1 taken along the line 2-2 of FIG. 1;

DETAILED DESCRIPTION OF EMBODIMENTS OF THE INVENTION

Figure 5:
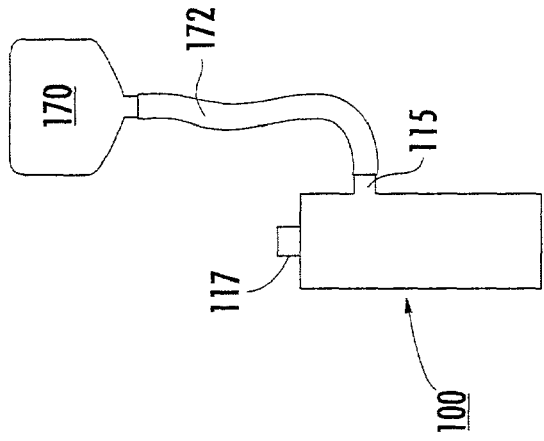
FIG. 5 is a side-elevational view of the device of FIG. 1, illustrated with an associated culturing medium supply according to embodiments of the present invention.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. In the figures, layers, components or regions may be exaggerated for clarity.

The devices and methods of the present invention may be used to detect the presence of microorganisms in clinical specimens, such as blood or other body fluids, and in non-clinical specimens such as food, juices, cosmetics, shampoos, pharmaceuticals or consumer products, by culturing the specimens with a growth or culturing medium in a container of a device according to the invention. The specimen may be filtered through a filter disposed in the container to capture a sample including microorganisms from the specimen. The presence and the identification of microorganisms may be determined by, for example, detecting or measuring changes in the pH of the specimen or the production of $CO_2$ within the specimen using a sensor disposed in the container. Thus, the devices and methods may provide a non-invasive means for detecting the presence of microorganisms in specimens by measuring an increase in metabolic byproducts produced by the microorganisms (directly or indirectly). Moreover, the culturing medium and the filter may be sterilized and maintained sterile. Further, the container may be effectively sealed and the integrity of the seal maintained during the evaluation process.

With reference to FIGS. 1 and 2, an integrated filtration and detection device according to the present invention is shown therein and generally designated by reference number 100. The device 100 may be used to filter a sample of microorganisms from a volume of a specimen selected for analysis and also to detect the growth of the microorganisms without directly handling the filter or exposing the filter, the specimen or the sample to contamination. Furthermore, the device 100 is adapted for convenient and effective use with electronic and automated measuring apparatus reducing labor costs and the risk of inadvertent process-induced contamination. The device 100 may be sealable and sterilizable. Moreover, the device 100 may be disposable after a single use.

Turning to the construction of the device 100 in more detail, the device 100 includes a container 110. The container 110 may be formed of an economic or inexpensive material. Preferably, the container 110 is formed of a material which may be effectively sterilized and sealed using conventional means. More preferably, the container 110 is formed of polycarbonate or other plastic.

The container defines an interior chamber 112 and has first and second opposed ends 110A and 110B. A fitting 115 extends outwardly between the ends 110A, 110B and defines an inlet 116, which fluidly communicates with the chamber 112. A fitting 117 extends downwardly from the end 110A and defines an outlet 118, which fluidly communicates with the chamber 112. The container 110 includes an end wall 114 on the end 110B. Preferably, at least the end wall 114 of the container 110 is translucent or transparent. Optionally (not shown), the container 110 may be further provided with a vent port communicating with the chamber 112. Preferably, the chamber 112 has a volume of between about 10 milliliters and 1 liter.

A sensor 120 is secured to the end wall 114 such that a surface 122 of the sensor 120 (FIG. 2) is in fluid communication with the chamber 112. The sensor 120 may be any suitable sensor for detecting or indicating a change in the chamber 112 caused by microbial growth. Suitable sensors and methods and materials for forming the same are disclosed in U.S. Pat. No. 5,856,175 to Thorpe et al. and U.S. Pat. No. 5,858,769 to DiGuiseppi et al., the disclosures of which are hereby incorporated herein by reference in their entireties. The following sensors may be advantageously employed, but are not exhaustive or exclusive of the types of sensors which may be used in the invention.

As discussed below, a culturing medium may be added to the specimen. The culturing medium may be specially formulated to enhance the production of certain microbial metabolic products. These microbial metabolic products may be detected by the sensor 120. The sensor 120 may comprise a solid composition or membrane (also referred to hereinbelow as an attachment or support medium), with an indicator medium immobilized on or within it. Suitable sensors for use as the sensor 120, in various forms, include: a) a suspension of a solid particulate indicator medium immobilized within an immiscible fluid; b) a suspension of a solid particulate indicator medium immobilized within a polymer that is then cured; c) a suspension of a liquid indicator medium impregnated or coated onto a solid support and immobilized within an immiscible fluid; d) a suspension of a liquid indicator medium impregnated or coated onto a solid support and immobilized within a polymer that is then cured; e) an emulsion of a liquid indicator medium in an immiscible fluid; f) an emulsion of a liquid indicator medium in a polymer that is then cured; and g) a membrane and an indicator medium, the indicator medium being selected for its ability to exhibit a detectable change when exposed to byproducts of an organism's metabolic activity.

The sensor 120 is preferably located flush against the inside surface of the container 110. Preferably, the end wall 114 is transparent or translucent such that the indicator medium is visible from outside. The sensor 120 may be affixed to the container 110 to prevent cells, proteins, other solids or other opaque or colored components from getting between it and the container surface. In certain embodiments, the sensor 120 is separated from the specimen and its growth medium by a membrane, a viscous layer, or a solid layer that permits the passage of gas molecules but prevents passage of ions.

The nutritional components that make up a complex microbial medium influence the metabolic pathways used by microorganisms. Organic acids, bases and various gases are produced in proportions dependent on the nutrients available. These products also vary from species to species of microorganism. The presence of these products in the liquid medium can change its pH. The sensor 120 used in the invention may contain pH sensitive indicators that give a measurable change in response to a pH change in the environment. In the embodiment in which the pH sensor is covered by a gas-permeable, ion-impermeable membrane, the presence of gases that affect the pH of the indicator, such as $CO_2$ or ammonia, may be measured. Thus, microbial growth can be detected either by changes in pH of the liquid culture medium or by measurement of gases dissolved in the medium, both indications being caused by metabolic gaseous products produced by microorganisms. Carbon dioxide is a universal metabolite produced by all organisms and, therefore, is the preferred metabolite for detection of microbial growth.

$CO_2$ and pH sensors as used for the sensor 120 may share two common components, a molecular species useful as a pH indicator and an attachment/support medium. The pH indicator can be attached either covalently or non-covalently to the support medium. Alternatively, the indicator can be encapsulated within a polymer matrix such as an indicator solution being emulsified within a polymer matrix prior to curing, or particles of solid indicator being suspended within a polymer matrix, which is then cured.

Also, the indicator can be attached to the solid support medium, for example, by soaking or impregnating the support medium with an indicator solution and then drying it. The support medium may be a membrane such as a nylon membrane. The dried, impregnated support medium can then be reduced to a fine powder, if needed, and blended with an immiscible fluid, such as polymer or a viscous fluid, forming a suspension sensor. In certain embodiments, the polymer can be cured. In other embodiments, a suspension sensor can be made by combining a solid indicator in particulate or granular-type form with an immiscible fluid, again, such as polymer, and then curing if needed.

To perform as a $CO_2$ sensor, the sensor 120 must be able to react with the byproducts of the microorganisms. The $CO_2$ sensor has a third component, a semipermeable substance that completely separates the indicator membrane from the specimen and growth medium. The semi-permeable layer may be a separate membrane, alternatively, the cured polymer adjacent to the specimen and growth medium may form an integral semi-permeable membrane. These sensors may be affixed to the container 110 with an appropriate adhesive or as an indicator emulsified within a polymer matrix cured in situ.

A variety of different fluorescent and visible pH indicators can be used as the active molecular species in pH or $CO_2$ sensors. They should have acceptable dynamic pH ranges and wavelength changes that are readily detectable by front surface fluorescence or reflectance technologies.

Preferably, sensors for detecting pH changes in the culture medium according to the invention exhibit a change in measurable properties such as fluorescence intensity or visible color at least over a pH range of about 5.0 to about 8.0. Preferably, indicators for the $CO_2$ sensors exhibit a change in measurable properties such as fluorescence intensity or visible color at least between about pH 13 and about 5, and more preferably between about pH 13 to about 9, in order to detect changes in $CO_2$ concentration.

Preferably, the pH indicators belong to the xanthene, phenolphthalein and phenolsulfonphthalein groups. Examples of these include fluorescein, coumarin, phenolphthalein, thymolphthalein, bromothymol blue, thymol blue, xylenol blue and α-naphthol benzein.

The attachment/support medium can be a substance such as cellulose, to which a pH indicator can be covalently attached using organic reactions. Non-covalent attachment of pH indicators can be achieved using ionic support materials, such as nylon membranes that have a positive or negative zeta potential. Other ionic support materials that can be used are positive or negatively charged ionic resins, such as diethylamino ethyl (DEAE) resin or DEAE cellulose. Pretreatment of the support material with a protein may be required if the indicator membrane is to be in direct contact with the microbial growth medium.

The pH indicator sensors directly detect pH changes due to the pH environment of the microbial growth medium. However, these sensors 120 can be made to selectively react to gases (e.g., carbon dioxide, ammonia) in the liquid growth medium by covering them with a selectively semi-permeable composition or membrane, such as silicone, latex, teflon, or various plastics characterized by the capacity to selectively permit the diffusion of a gas while preventing the passage of ions. For sensors 120 comprising indicator encapsulated within a polymer matrix, such as emulsion or suspension sensors, the polymer forming the matrix can act as the semipermeable barrier that permits the passage of gases but not ions.

In the emulsion sensor embodiments of encapsulated indicator, the $CO_2$ sensor is preferably comprised of four components. The first component is a visual or fluorescent pH indicator, which is preferably reactive at least at the pH range between 6 and 10. Examples of indicators meeting these criteria are bromothymol blue, thymol blue, xylenol blue, phenolphthalein, coumarin, and fluorescein. The second component is sodium hydroxide or an equivalent base, which maintains an optimal pH environment for detection of $CO_2$ by the selected pH indicator. The third component is glycerol or an equivalent emulsifier, which can produce droplets of indicator solution emulsified within the uncured polymer. The fourth component is the uncured polymer such as silicone, which maintains a proper environment for the indicator. Any polymer can be used that does not affect the chemical activity of the indicator, either from its own chemical or physical properties or its requirements for curing, as long as it is permeable to gases but not ions, and does not have these properties altered when subjected to sterilization. Other silicone polymers that are also satisfactory are those that are cured by high temperature, by catalytic activity, or by ultraviolet vulcanization. An emulsion is prepared from the four components and the polymer is cured to form a semipermeable matrix around the droplets of pH indicator, which permits selective diffusion of $CO_2$ and other gases from the liquid microbial growth medium, resulting in a measurable change in the indicator. The sensor can be prepared separately, such as in a mold, cured, and then attached to the container 110 with an appropriate adhesive, such as a silicone adhesive. Alternatively, and preferably, the sensor 120 is formed on the end wall 114 of the container 110 and cured in situ.

Similarly, the $CO_2$ sensor can be manufactured as a suspension, incorporating many of the same elements as above. Generally, a suspension is defined as a system in which very small particles are more or less uniformly dispersed in a liquid medium. If the particles are small enough to pass through filter membranes, the system is a colloidal suspension. If the particles are larger than colloidal dimensions they tend to precipitate, if heavier than the suspending medium, and to agglomerate and rise to the surface, if lighter. (Hawley's Condensed Chemical Dictionary, edited by N. Sax and R. Lewis, Sr., 11th edition, 1987, N.Y., N.Y.)

A granular or particulate-type of indicator medium can be blended or mixed with a suitable immiscible fluid, whereby the result is a suspension of the solid indicator medium in the fluid. If a polymer is used as the fluid, it can be cured after forming the suspension to produce a solid suspension sensor.

By adding a support medium to an indicator solution, another type of suspension sensor can be produced. In this embodiment, the indicator medium is a solution, such as a suitable soluble indicator medium dissolved in a NaOH solution, which is attached to a solid support medium, for example, by impregnating or coating the solid support medium. The indicator solid support medium is then dried, and can be reduced to a fine powder, for example by cutting or grinding, or used as is. The impregnated or coated support is blended with an immiscible liquid, such as a polymer, as above, forming a suspension. The suspension sensor can be used in the same way as the emulsion sensor above. As with the emulsion sensor, when the suspension sensor involves the use of a polymer that may need to be cured, it is preferable to form the suspension sensor directly in the container 110 and then cure it in situ. If so desired, a semipermeable material may be placed over the suspension sensor to separate the sensor from the liquid or solid contents of the container. For example, an overlay (not shown) of a semi-permeable polymer or immiscible liquid may be placed over the suspension sensor. Preferably, the overlay reflects light that passes through the sensor 120 and also protects the sensor 120 from direct contact with the liquid or solid contents of the container.

An exemplary sensor 120 may be formed of xylenol blue, NaOH, borate buffer and Triton X-100.

As a further alternative, the sensor 120 may be an $O_2$ sensitive fluorescent sensor. As microbes in the chamber 112 grow, they consume $O_2$ thereby reducing the amount of $O_2$ at the sensor 120. The fluorescence of the sensor, which is quenched by $O_2$, increases as the $O_2$ concentration decreases. Microbial growth can thereby be detected by the increase in fluorescence. For example, the sensor 120 may be a sensor as disclosed in U.S. Pat. No. 5,998,517 to Gentle et al. and U.S. Pat. No. 5,567,598 to Stitt et al.

Another type of sensor that may be used for the sensor 120 includes a piezoelectric apparatus (not shown), such as a piezoelectric strip, that is attached to the container 110. The signal from the piezoelectric apparatus can be automatically zeroed when the container 110 and its contents reach a given or selected temperature (e.g., an incubation temperature). The piezoelectric apparatus can be constructed and/or mounted such that it is distorted by the pressure of the metabolic products produced by microorganisms. The electrical signals generated from this distortion can be measured to monitor the biological activity inside the container 110.

Referring again to FIGS. 1 and 2, a collection filter 130 is mounted adjacent the end 110A of the container 100 and between the inlet 116 and the outlet 118. In certain embodiments, the filter 130 is constructed and mounted such that substantially all fluid passing from the inlet 116 to the outlet 118 passes through the filter 130. As shown, the filter 130 is adapted to collect all or a substantial portion of potential or anticipated microorganisms from a specimen while allowing the carrier fluid of the specimen to pass through the filter 130. In FIG. 1, the filter extends across the entire cross-sectional area of the chamber. Preferably, the filter 130 is a microporous filter configured to capture microorganisms therein while passing soluble components of the specimen, wash fluid or culturing medium. The microporous filter may be hydrophobic or hydrophilic. Preferably, the pores of the microporous filter are no larger than 0.4 micron, and, more preferably, are between about 0.2 and 0.4 micron. Suitable filter membranes for the filter 130 include product no. GSWP 0500 (hydrophilic, cellulose-based, for aqueous solutions) and product no. FGCP 04700 (hydrophobic, Teflon™-based, for solvent solutions), each available from Millipore Corporation of Bedford, Mass.

Figure 3:
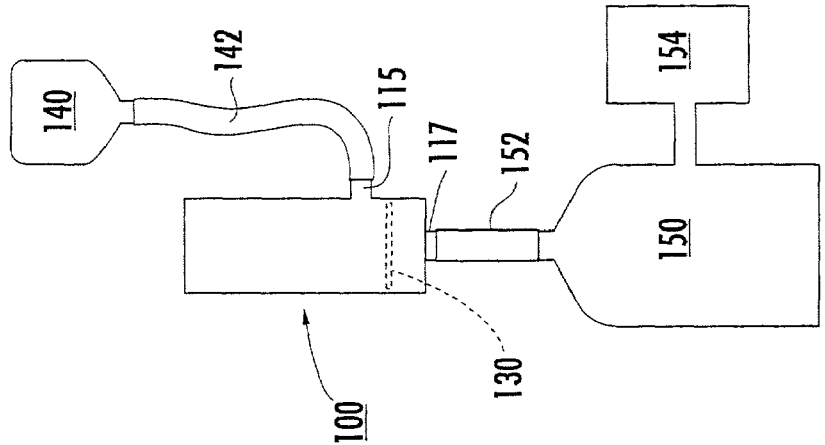
FIG. 3 is a side elevational view of the device of FIG. 1, illustrated with an associated specimen supply, an associated waste receptacle and an associated pump according to embodiments of the present invention.
Figure 7:
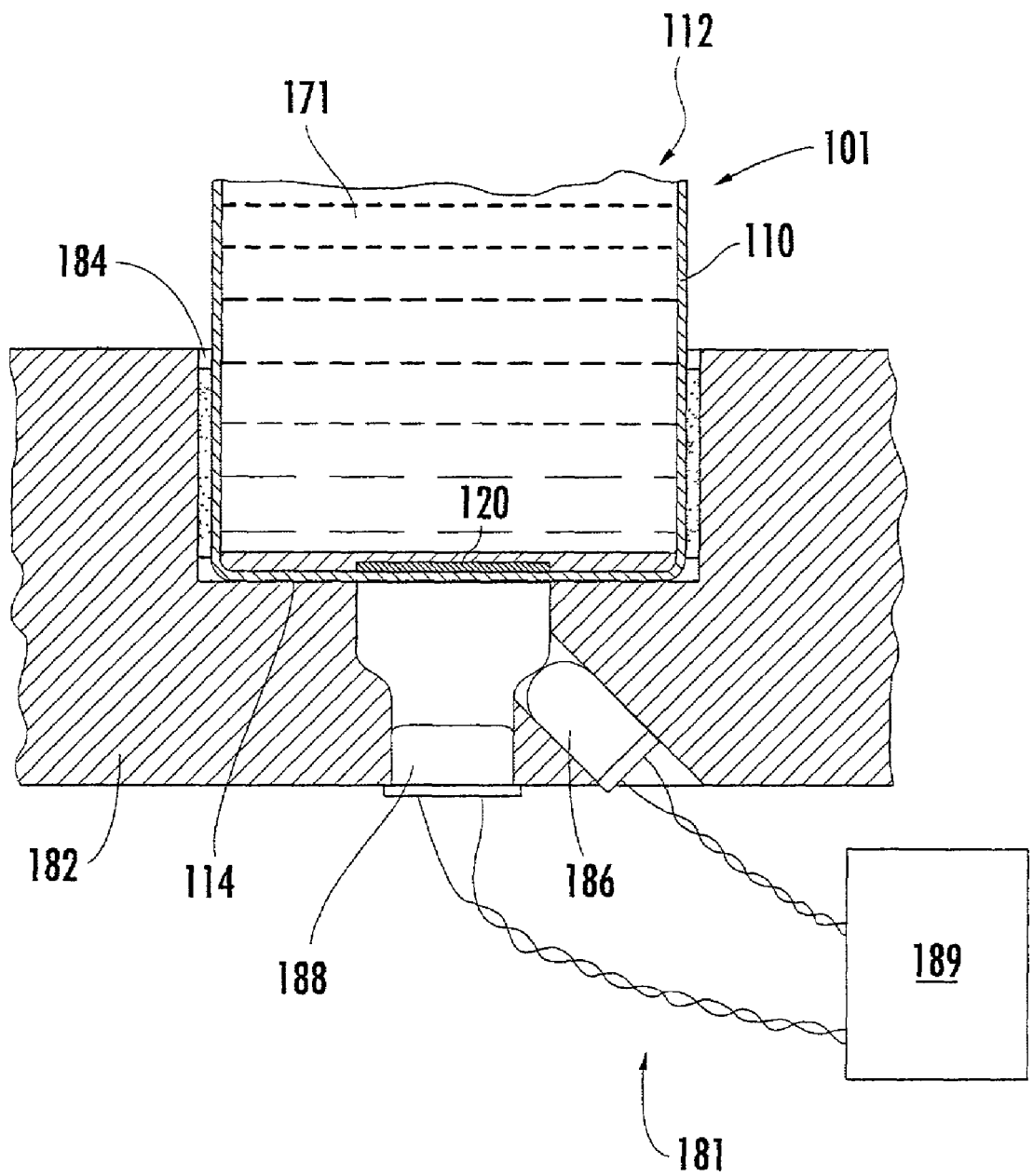
FIG. 7 is a fragmentary, cross-sectional view of a measuring apparatus and the sample assembly of FIG. 6 mounted therein.

With reference to FIGS. 3-7 and the flow chart of FIG. 8, the device 100 may be used in the following manner to filter and detect the growth of microorganisms from a specimen. Initially, the device 100 (including the filter 130 and the sensor 120) as well as the tubing 142, 152, 162 and 172 described below may be sterilized, for example, using an autoclave, chemical disinfectant or radiation. As shown in FIG. 3, a supply 140 of the fluid (typically liquid) specimen is connected to the fitting 115 of the device 100 by suitable tubing 142. The specimen may be, for example but not limited to, potable water, beverage or food products, pharmaceuticals and their production intermediates, or parenteral fluids.

With further reference to FIG. 3, a waste receptacle 150 is connected to the fitting 117 by suitable tubing 152. The waste receptacle 150 is in turn operatively connected to a fluid flow source such as a vacuum source 154 which may be a pump. Alternatively, a pump (e.g., a peristaltic pump) may be provided at the tubing 142. Other flow sources may also be used. For example, the specimen may be gravity fed. The vacuum source 154 is operated to create a vacuum at the inlet 116 (FIG. 2) of the device 100. The specimen is thereby drawn, sequentially, from the supply 140, through the tubing 142, through the inlet 116, through the filter 130, through the outlet 118 (FIG. 2), through the tubing 152 and into the waste receptacle 150 (Block 192 of FIG. 8). As the specimen passes through the filter 130, microorganisms (if present) in the specimen are collected on the filter 130, captured or trapped (i.e., inhibited or prevented) from passing with the remainder of the specimen to the waste receptacle 150. These captured microorganisms constitute a sample which may be used to evaluate for the presence of microbes in the specimen supply 140. Advantageously, the concentration of microorganisms in the sample may be substantially increased as compared to the concentration of the microorganisms in the specimen so that changes caused by microbial growth will be detected earlier and thereby more effectively. Preferably, substantially all of the specimen not captured in the filter 130 is drawn out of the chamber 112. Typically, the volume of the filtered specimen may be in the range of between about 100 milliliters and 10 liters.

Figure 4:
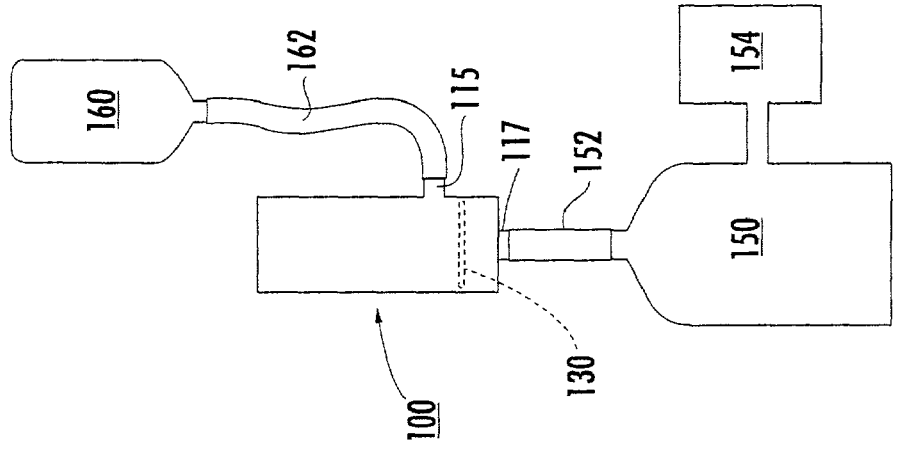
FIG. 4 is a side elevational view of the device, waste receptacle and pump of FIG. 3, illustrated with an associated wash fluid supply according to embodiments of the present invention.

With reference to FIG. 4, an optional wash step may be conducted. More particularly, a wash fluid supply 160 may be connected to the fitting 115 by suitable (preferably sterile) tubing 115. The wash fluid is drawn or directed sequentially through the inlet 116, the filter 130 and the outlet 118 and into the waste receptacle 150 by the vacuum source 154 (Block 193). The wash step may be used, for example, to wash preservatives or other microbe growth inhibitors from the container 110, the filter 130 and the captured sample. Suitable wash fluids may include, for example, growth media, buffered salt solutions, detergents or emulsifiers and are sterilized prior to introduction into the chamber 112.

Thereafter, and preferably after the wash fluid is drained from the chamber 112 (not shown in FIGS. 3-5), a supply 170 of culturing medium or broth is connected to the fitting 115 by suitable tubing 172 (FIG. 5). Preferably, the tubing 172 and the culturing medium are sterile. Preferably, the device 100 is inverted as shown in FIG. 5. Thereafter, the culturing medium is fed, for example, by gravity feed, from the supply 170, through the tubing 172, through the inlet 116 (FIG. 2) and into the chamber 112 (Block 194 of FIG. 8). The outlet 118 (FIG. 2) serves as a vent for the air in the chamber 112 displaced by the culturing medium. The culturing medium is preferably sterilized prior to introduction to the chamber 112. A one-way valve may be used to inhibit the entry of fluids or air as needed (not shown).

Figure 6:
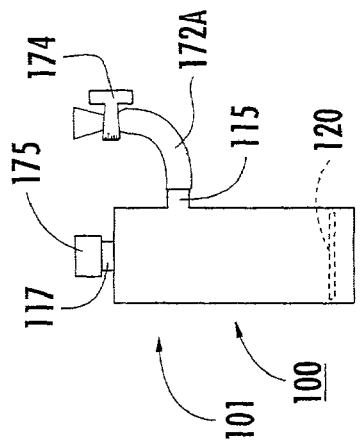
FIG. 6 is a side-elevational view of a sample assembly including the device of FIG. 1, along with an associated length of tubing and a clamp, wherein the device contains the culturing medium according to embodiments of the present invention.

With reference to FIG. 6, a cap 175 (preferably a screw cap) may be placed over the fitting 117. A suitable clamp 174 is clamped over the tubing 172. The tubing 172 is then cut above the clamp 174 such that a portion 172A of the tubing 172 remains attached to the fitting 115. In this manner, the tubing 172A and the clamp 174 form a secure and sterile closure to the inlet 116. The device 100, the tubing 172A, the clamp 174, the contained culturing medium 171 and the captured microorganism sample together form a sample assembly 101 (FIG. 6). Other closure or sealing techniques can also be used such as adhesives, heat to close the tube, tie wraps and the like.

Figure 8:
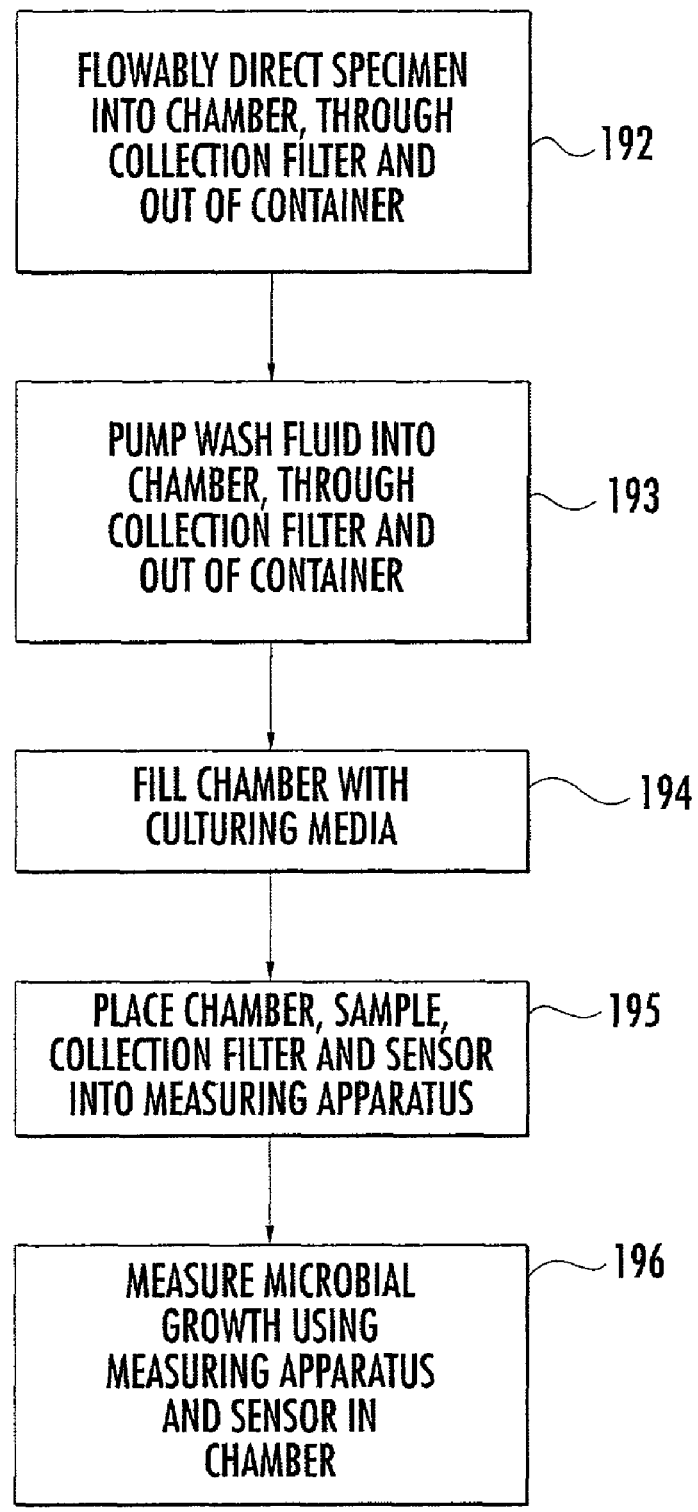
FIG. 8 is a block diagram representing a method of collecting and detecting the growth of microorganisms in a specimen according to embodiments of the present invention.

The sample assembly 101, or a plurality of sample assemblies 101, may then be placed in a suitable measuring apparatus 180 (Block 195 of FIG. 8). The measuring apparatus may be an automated apparatus as described in U.S. Pat. No. 5,858,769 to DiGuiseppi et al. or as described in U.S. Pat. No. 5,164,796 to DiGuiseppi et al., the disclosures of which are hereby incorporated herein by reference in their entireties. The sample assembly 101 may be inserted into a slot 184 in a platform 182 for evaluation by a detector assembly (generally designated 181). The detector assembly 181 includes a photoemitter 186 and a photodetector 188, each of which is operatively connected to an analysis apparatus 189. The photoemitter 186 directs light onto the sensor 120 and the light is reflected back to the photodetector 188. The analysis apparatus 189 evaluates signals from the photodetector, for example, in the manner described in U.S. Pat. No. 5,164,796. The microorganism analysis results can be automated and results generated without requiring human evaluation.

In the foregoing manner, the measuring apparatus 180 detects changes in the sensor 120 and thereby measures microbial growth in the chamber 112 (Block 196). For example, the measuring apparatus 180 may detect changes in the color or fluorescence of the sensor through the transparent end wall 114, such color or fluorescence changes being caused by pH changes, the generation of $CO_2$ and/or the consumption of $O_2$ in the chamber 112 from microbial growth. For example, the measuring apparatus 180 may include instruments as described in U.S. patent application Ser. Nos. 07/322,874, filed on Apr. 3, 1989 (now abandoned), and 07/351,476, filed on May 15, 1989 (now abandoned), U.S. Pat. No. 4,945,060 and U.S. Pat. No. 5,856,175, which are incorporated herein by reference. The apparatus 180 may include a visible light reflectometer that monitors the color change of the sensor. Solid state illuminators and detectors may be used. Incandescent and arc lamp sources of illumination may also be used in conjunction with mirrors, lenses, optical fibers, and other means of directing the light to the sensor. In order to allow continuous monitoring of all samples, it is preferred to have a detector for each sample. The outputs of the various detectors may be compiled by a computer, and curves characteristic of the quantity and rate of change of pH or $CO_2$ or $O_2$ concentration of various samples may be generated. The computer may also perform the necessary analysis to evaluate the characteristics developed and to determine the presence or absence of developing microbial cultures. The apparatus 180 and/or additional apparatus may heat and/or agitate the device 100 to incubate or otherwise promote growth of the sample microorganisms.

Figure 9:
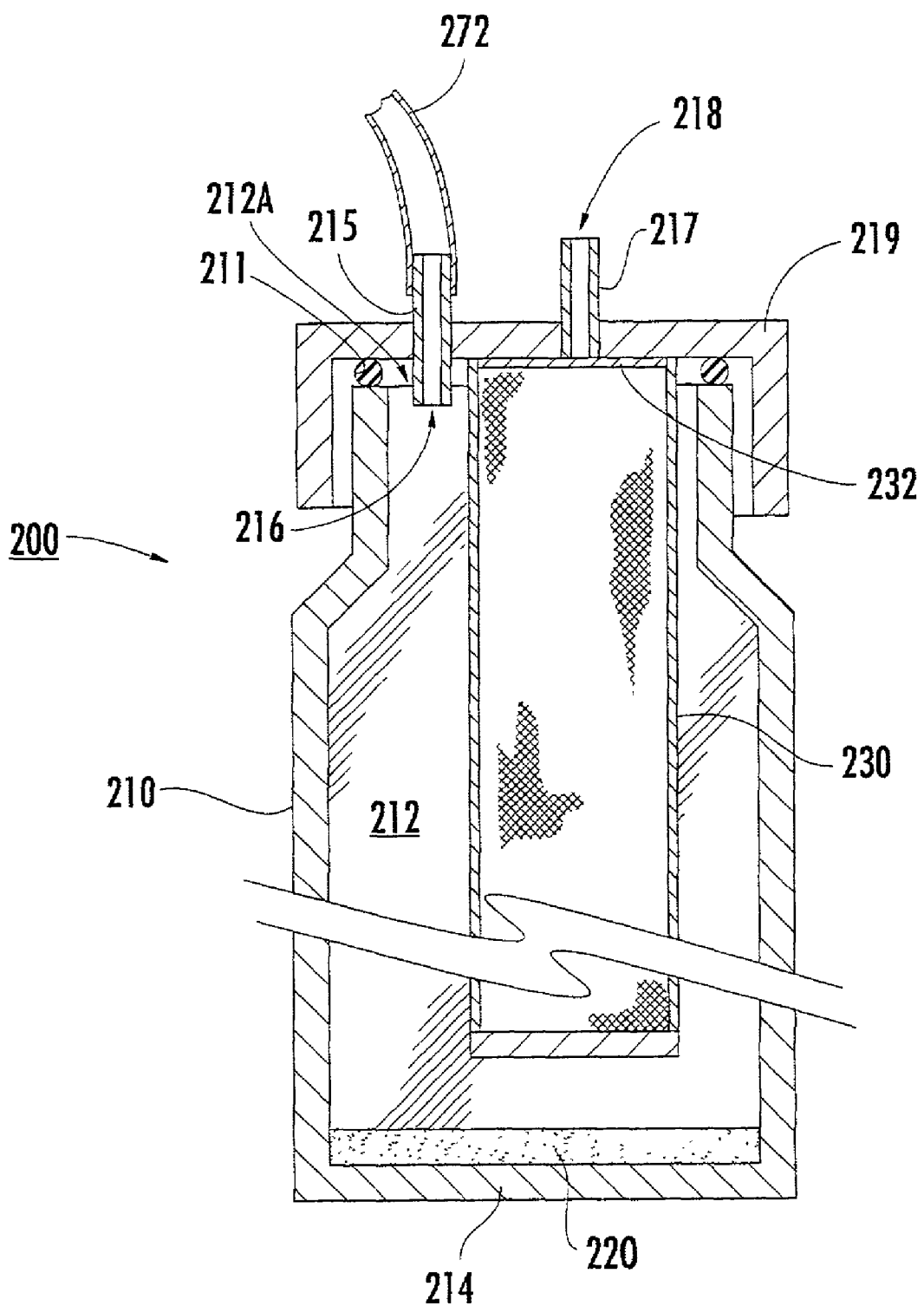
FIG. 9 is a cross-sectional view of an integrated filtration and detection device according to further embodiments of the present invention.

With reference to FIG. 9, an integrated filtration and detection device 200 according to further embodiments of the present invention is shown therein. The device 200 includes a container body 210 defining an interior chamber 212. The container body 210 has an end wall 214 and defines an opening 212A communicating with the chamber 212. Preferably, the end wall 214 is transparent.

An end cap 219 is disposed over the opening 212A. An O-ring 211, gasket, adhesive or other sealant may be used to provide a seal between the cap 219 and the container body 210. A second fitting 215 extends through the cap 219 and defines an inlet 216. A second fitting 217 extends through the cap 219 and defines an outlet 218.

A radial flow filter 230 is secured to the underside of the cap 219. Preferably, the filter 230 is a microporous filter. The filter 230 is preferably constructed and mounted such that substantially all fluid passing from the inlet 216 to the outlet 218 passes through the filter medium of the filter 230. A second filter 232 can be positioned between the filter 230 and the outlet 218. Preferably, the second filter 232 is also a microporous filter.

A sensor 220 may be secured to the end wall 214 (or other desired externally visible location). The sensor 220 may be any of the sensors and may be mounted in any of the ways as described above with regard to the sensor 120.

The device 200 may be used in substantially the same manner as the device 100 with connections being made with the fittings 215 and 217 in place of the fittings 115 and 117, respectively. It may be desirable to invert the device 100 during the steps of filtering the specimen and introducing the wash fluid. Tubing 272 corresponding to the tubing 172 may be cut and clamped or secured in the same manners described above to provide a secure and sterile closure. The filter 232 serves to prevent or inhibit entry of contaminants into the chamber 212 through the outlet 218. Additionally, a cap may be placed over the fitting 215 and/or the fitting 217. Also, either or both of the fittings 215, 217 may be provided with a one-way valve.

As a further alternative, the sensor 220 may be secured to or may be made part of the cap 219 (not shown). The cap or a section thereof may be transparent so that, in the case of a sensor of the type that changes color, the changes in the color of the sensor 220 may be evaluated through the end cap 219. The end cap 219 may be made of a material, such as a polymer, which contains encapsulated indicator micelles.

The sensors 120, 220 may be relocated in the container 110 or container body 210. In the case where color changing sensors are employed, each container should include at least a transparent (or translucent) section adjacent the sensor 120, 220. Alternatively, the sensors 120, 220 may each be formed (e.g., molded) as an integral part of the respective container 110 or container body 210. The sensors 120, 220 may also be placed outside the container, as long as sealed (from the environment) fluid communication means are provided for the metabolic products of the microorganisms or the growth medium containing the specimen to react with the sensor.

The foregoing devices 100, 200 and methods and variations thereof as described above provide a number of advantages. The sample may be collected, incubated and evaluated without breaking the sterility barrier. The devices and methods serve to combine certain steps of preparing a sample and detecting microbial growth in the sample. The devices and methods eliminate or reduce handling of various components, thereby providing enhanced convenience and greater security against inadvertent contamination during testing and evaluation. In particular, the sample, the filter, the sensor and adjacent interior portions of the container are protected from contamination, thereby reducing or eliminating the risk of a false positive caused by microorganisms not introduced from the original specimen.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. An integrated filtration and detection device for collecting and detecting the growth of microorganisms in a specimen, said device comprising:
  a) a container including a side wall and a fixed end wall defining a chamber therein and having an inlet and an outlet in fluid communication with said chamber, wherein said end wall defines a continuous closed surface that is continuous with said side wall and free of openings;
  b) a filter for filtering fluids, said filter mounted in said chamber between said inlet and said outlet; and
  c) a sensor mounted in said chamber parallel to and against said end wall of said chamber, said sensor operative to exhibit a change in a measurable property thereof upon exposure to changes in said chamber due to microbial growth;
  wherein said container has a transparent section and changes in said measurable property of said sensor are detectable through said transparent section; and said sensor and said filter are disposed at opposed ends of said chamber.

2. The device of claim 1 wherein said container is unitary and said inlet and said outlet are the only openings into said container communicating with said chamber.

3. The device of claim 2 wherein:
  said device has an operative testing orientation and, when said device is in said operative testing orientation, said sensor resides at a lower end of said chamber and below said filter; and
  wherein, when said device is in said operative testing orientation, said inlet and said outlet are each located above said sensor.

4. The device of claim 1 wherein said device has an operative testing orientation and, when said device is in said operative testing orientation, said sensor resides at a lower end of said chamber and below said filter.

5. The device of claim 1 wherein said filter is a microporous filter.

6. The device of claim 1 wherein said filter is a radial flow filter.

7. The device of claim 1 wherein said sensor is responsive to at least one of a change in pH and the presence of $CO_2$.

8. The device of claim 1 wherein said sensor is operative to change color in response to at least one of a change in pH and the presence of $CO_2$ in said chamber.

9. The device of claim 8 wherein changes in the color of said sensor are detectable through said transparent section.

10. The device of claim 1 wherein said sensor is bonded to said interior surface of said container.

11. The device of claim 1 wherein said container is formed of a plastic.

12. The device of claim 1 wherein said container includes:
a container body having an end opening opposite said end wall on which said sensor is mounted; and
an end cap secured over and sealing said end opening;
wherein said inlet and said outlet are formed in said end cap.

13. The device of claim 12 including an O-ring seal between said container body and said end cap.

14. An integrated filtration and detection product for collecting and detecting the growth of microorganisms in a specimen, said product comprising:
a container defining a chamber therein and having an inlet and an outlet in fluid communication with said chamber;
a liquid culturing medium disposed in said chamber;
a filter for filtering fluids, said filter mounted in said chamber between said inlet and said outlet; and
a sensor mounted in said chamber parallel to and against an end wall of said chamber, said sensor operative to exhibit a change in a measurable property thereof upon exposure to changes in said chamber due to microbial growth;
wherein said container has a transparent section and changes in said measurable property of said sensor are detectable through said transparent section; and said sensor and said filter are disposed at opposed ends of said chamber;
wherein said sensor resides at a lower end of said chamber and below said filter; and
wherein said liquid culturing medium is disposed in said lower end of said chamber and contacts said sensor in said lower end of said chamber.

15. The product of claim 14 wherein:
said container includes a side wall defining the chamber;
said end wall is fixed and defines a continuous closed surface that is continuous with the side wall and free of openings; and
said inlet and said outlet are each located above said sensor.

16. The product of claim 14 wherein said chamber is fully sealed.

17. The product of claim 14 wherein said device has an operative testing orientation and, when said device is in said operative testing orientation, said sensor resides at a lower end of said chamber and below said filter.

18. The product of claim 14 wherein said filter is a microporous filter.

19. The product of claim 14 wherein said filter is a radial flow filter.

20. The product of claim 14 wherein said sensor is responsive to at least one of a change in pH and the presence of $CO_2$.

21. The product of claim 14 wherein said sensor is operative to change color in response to at least one of a change in pH and the presence of $CO_2$ in said chamber.

22. The product of claim 21 wherein changes in the color of said sensor are detectable through said transparent section.

23. The product of claim 14 wherein said sensor is bonded to said interior surface of said container.

24. The product of claim 14 wherein said container is formed of a plastic.

25. The product of claim 14 wherein said container includes:
a container body having an end opening opposite said end wall on which said sensor is mounted; and
an end cap secured over and sealing said end opening;
wherein said inlet and said outlet are formed in said end cap.

26. A system for detecting the growth of specimen in a specimen, said system comprising:
a) an integrated filtration and detection device comprising:
a container including a side wall and a fixed end wall defining a chamber therein and having an inlet and an outlet in fluid communication with said chamber, wherein said end wall defines a continuous closed surface that is continuous with said side wall and free of openings;
a filter for filtering fluids, said filter mounted in said chamber between said inlet and said outlet; and
a sensor mounted in said chamber parallel to and against said end wall of said chamber, said sensor operative to exhibit a change in a measurable property thereof upon exposure to changes in said chamber due to microbial growth;
wherein said container has a transparent section and changes in said measurable property of said sensor are detectable through said transparent section; and said sensor and said filter are disposed at opposed ends of said chamber; and
b) a measuring apparatus operable to detect the measurable property of said sensor through said transparent section.

27. A system for detecting the growth of microorganisms in a specimen, said system comprising:
a) an integrated filtration and detection product comprising:
a container defining a chamber therein and having an inlet and an outlet in fluid communication with said chamber;
a liquid culturing medium disposed in said chamber;
a filter for filtering fluids, said filter mounted in said chamber between said inlet and said outlet; and
a sensor mounted in said chamber parallel to and against an end wall of said chamber, said sensor operative to exhibit a change in a measurable property thereof upon exposure to changes in said chamber due to microbial growth;
wherein said container has a transparent section and changes in said measurable property of said sensor are detectable through said transparent section; and said sensor and said filter are disposed at opposed ends of said chamber;
wherein said sensor resides at a lower end of said chamber and below said filter; and
wherein said liquid culturing medium is disposed in said lower end of said chamber and contacts said sensor in said lower end of said chamber; and
b) a measuring apparatus operable to detect the measurable property of said sensor through said transparent section.

* * * * *